United States Patent [19]

Hoek

[11] 4,364,938
[45] Dec. 21, 1982

[54] PRODUCTION OF IMMUNOGENIC PRODUCTS AND TREATMENT OF ALLERGIC REACTIONS THEREWITH

[76] Inventor: Gijsberk T. Hoek, Parklaan 81, Haarlem, Netherlands, 2001HB

[21] Appl. No.: 234,303

[22] Filed: Feb. 13, 1981

[51] Int. Cl.$^3$ ..................... A61K 39/35; A61K 39/36
[52] U.S. Cl. ......................................... 424/88; 424/9; 424/85; 424/91
[58] Field of Search ........................... 424/9, 85, 88, 91

[56] References Cited
U.S. PATENT DOCUMENTS 2,150,131  3/1939  Rockwell ............................. 424/91
2,500,145  3/1950  Ferguson ............................ 424/91

OTHER PUBLICATIONS

Merck Index, Merck and Co., Rahway, N.J., 9th Ed., 1976, p. 7613, No. 7610.

Primary Examiner—Anna P. Fagelson

[57] ABSTRACT

A method for the production of immunogenic products useful in the therapeutic treatment of allergic conditions in patients, comprising the solvent extraction from allergenic substances of the solvent soluble components thereof to obtain the residue of extraction which may be employed as an immunogenic material possessing reduced allergenicity. If desired, the thus obtained residue of extraction may be further treated with a suitable ketone, aldehyde, lactone or epoxide to yield a product having enchanced immunogenic properties and reduced toxicity.

7 Claims, No Drawings

PRODUCTION OF IMMUNOGENIC PRODUCTS AND TREATMENT OF ALLERGIC REACTIONS THEREWITH

This invention relates to a novel method of producing immunogenic substances which are useful in the therapeutic treatment of patients suffering from allergic disorders. More particularly, this invention relates to a method of preparing substances possessing immunogenic properties, which substances may be administered to patients suffering from allergic disorders, for the purpose of therapeutically treating such disorders in a safe and efficient manner.

Patients suffering from allergic disorders usually exhibit various untoward reactions when they come in contact with the substances to which they are allergic. The untoward reactions which are manifested by these patients can vary depending upon the intensity of contact with the substance to which they are allergic, the sensitivity levels of the patient himself, and the type or character of the substance to which the patient is sensitive. Among the various substances to which patients have been shown to be allergic, that is substances to which they are hypersensitive are such substances as pollens, molds, epithelia, including animal danders, house dusts and other inhalants, yeasts and other like substances. Contact with one or more of these substances commonly called "allergens", to which the patient is hypersensitive can result in the patient's manifesting various allergic reactions including such respiratory tract reactions, such as rhinitis, asthma attacks, or airway obstructions, or ophthalmic reactions such as conjunctivitis, pruritis or edema of the eyelids, as well as other similar allergic reactions. The severity of the allergic reaction can vary from a very mild, transient reaction to one that is of long duration and disabling.

Heretofore, patients suffering from allergic reactions as a result of contact with allergens have been therapeutically treated by a hyposensitization method. This hyposensitization method is one which requires an extended period of treatment of the patient and is one that must be closely monitored since the risk of severe allergic reaction is great. In the practice of this hyposensitization method, it is first required to obtain an extract of the allergenic substance. This allergenic extract is prepared by obtaining a quantity of the allergen, for instance, in the case of pollenosis, i.e., hayfever sufferers, a quantity of pollen is obtained, and extracting this allergen with a solvent, for example, water. This solvent extract of the allergen, in this instance the aqueous extract of pollen, is a concentrate that may not be therapeutically employed as such, but must be diluted to employable concentrations by the addition thereto of suitable pharmacologically acceptable diluents. Dilutions of this concentrate may then be administered to the patient over an extended period in small, ever increasing doses on the theory that in response to the continued administration of increasing doses the body will create and build up its own protective immunogenic reaction to the antigenic material contained in the solvent extract and will eventually create its own antibodies and defenses which will protect the patient from any allergic reaction should he thereafter come into natural contact with the allergenic substance. The theory behind this hyposensitization method of treatment has been that all the antigenic substances which cause the allergic reaction in patients is contained in the solvent extract of the allergenic material, and therefore only such concentrated extracts may be employed to hyposensitize patients. It has always been held that the residue of the allergenic substance which remains after solvent extraction was inert and useless for therapeutic use, most of the antigenic material having been removed by solvent extraction.

While hyposensitization has generally been successfully employed in the treatment of allergic patients, it suffers from a number of disadvantages. Firstly, there is the risk of initiating untoward reactions after the administration of a dose of the sensitizing substance. Secondly, the extracts have a tendency to deteriorate fairly rapidly. Thirdly, by causing severe allergic reactions upon administration to certain patients, it is often very difficult to obtain or determine a dosage level that is protective and therefore effective dosage levels cannot be achieved in some cases. This last disadvantage is the most dangerous to the patient and can cause severe general allergic reactions to the hyposensitizing doses of extract administered to the patient. These allergic reactions can manifest themselves as uticaria, edema, erythema, or respiratory difficulties and in extreme cases as acute anaphylactic reactions which could result in the death of the patient.

I have now discovered a method to therapeutically treat patients suffering from allergic conditions which successfully immunizes the patient from allergic reactions while at the same time obviating the disadvantages of prior art methods and products. I have unexpectedly found that contrary to the precepts and teachings of the prior art, that while solvent extraction of certain allergenic substances does remove much of the antigenic substance, the residue remaining after said extraction possesses sufficient immunogenic properties against those reactions caused by exposure to allergenic substances, to permit its administration to patients for the treatment of allergic conditions. It appears that by the process of this invention it is possible to obtain a therapeutic product which retains sufficient immunogenic activity to protect the patient from subsequent allergic reactions, while at the same time the presence of the antigenic substances which heretofore caused the undesired allergic side effects and reactions of the prior art products, can be excluded, or substantially reduced.

The satisfactory practice of the instant invention requires that the immunogenic product to be employed herein be prepared, in accordance with the process of this invention. To produce the immunogenic product of this invention requires a number of steps beginning with a quantity of the allergenic material, to which the patient to be treated hereunder is allergic, as starting material. The allergenic material which may be employed in the practice of this invention are those substances to which the patient is allergic and which may be characterized as physically having cell walls or particle fractions which possess the desired immunogenic properties. Among the allergenic materials which may be satisfactorily employed in the practice of the invention are such allergy causing materials which possess the cell walls or particle fractions, as pollens, molds, epithelia, such as animal danders, yeasts, and other like allergenic materials having similar characteristics.

In the first step of the instant invention, those allergenic materials which may be employed in the practice hereof, are treated with a solvent so as to extract and remove therefrom the undersired antigenic substances which are soluble therein. The extraction of these undesired antigenic substances may be carried out in any manner known to accomplish this result, for example, continuous stirring or flushing of the allergenic materials in the presence of the selected solvent, ultrasonic treatment, or urea addition, and other like methods known in the art to be useful to accomplish these purposes. The solvents which may be satisfactorily employed in the extraction procedure may be any solvent in which the antigenic substances are soluble, depending upon the allergenic materials being extracted. Among the solvents which may satisfactorily be employed in the practice of this invention may be included such solvents as water, alcohols, glycerols, dimethyl sulfoxide, phenol and such other like solvent systems. In most instances it has been found that simple solvents, which are pharmacologically acceptable, i.e., water and alcohol provide very satisfactory results. The extraction procedure is carried out until most of the promptly soluble allergens are extracted into the solvent and the process repeated and/or continued until the residue of extraction remaining contains no more than 1:100 w/w of its original allergenic content.

After the solvent extraction of the allergenic materials has been completed, the solvent extract thus obtained is discarded and the extracted allergenic material residue, which is a new final product of this invention, may be administered either directly or in combination with a suitable adjuvant, such as, aluminum hydroxide, to patients in the therapeutic treatment of the allergic conditions from which they may be suffering. In some instances where further treatment of the allergenic residue final products of this invention may be desired to obtain a final product of sufficient immunogenecity and reduced toxicity, the thus obtained extracted residue may be further treated to obtain further final products of this invention.

In those instances where the residue is to be further treated in accordance with this invention, especially where the initial solvent extraction procedures were carried out with aqueous or alcohol or glycerol solvents, the allergenic residue may be directly further treated in accordance with this invention. However, where a non-aqueous solvent has been employed in the extraction process it is recommended that any remaining traces of the solvent be first removed from the extracted allergenic residue. This may be accomplished by thoroughly washing the extracted allergenic residue with water until substantially all the solvent is removed.

The resultant extracted allergenic residue may then be further treated in accordance with the methods of this invention. The extracted allergenic residue may then be further treated in such a manner as to denature the residue materials to such an extend so as to permit it to be employed in the therapeutic treatment of patients without the occurrence of allergic reactions. The denaturing process of this invention may be accomplished by a number of procedures. One such procedure involves the reaction of the extracted allergenic residue with an organic reactant for a sufficient time and under such conditions as will assure complete reaction to denature the material. This may be accomplished by reacting the allergenic residue with an organic reactant such as a ketone, aldehyde, lactone, urea, alkali, epoxide, acyl or aryl halogenates and other like substances for a sufficient time at a sufficient temperature and at a favorable pH level to yield the desired final denatured product. The organic reactants preferably employed in the practice of this invention may be such keytones or aldehydes, as $\beta$-propiolactone, formaldehyde, glutaraldehyde, or such other dialdehydes of up to six carbon atoms, which are reacted with the allergenic residue at a pH of from about 4.0 to 11.0 and preferably from about 7.5 to about 8.5 over a period of time which can extend from a few hours up to as much as about 2 months, until the reaction is complete.

The denatured product thus obtained may then be further treated to provide the final products of this invention. The final denatured material may first be washed to remove any unreacted chemical reactants. These final products may then be put up in final form for administration to the patients to be treated. Thus, these final products may be put up in saline solutions for injection, or they may be freeze dried for future reconstitution into injectable solutions at a later date, or they may be alum absorbed and administered in that form, all of said methods of preparing the final dosages being well known in the art for such purposes. The final products of this invention may be administered to the patient in a single dose or a series of doses over a period of time depending upon the requirements of the patient and the condition being treated. In the practice of this invention satisfactory results have been obtained when 0.01 mg. to 10.0 mg. of the final products of this invention have been administered.

The final compositions of this invention which are to be administered to the patients to be treated, may be made up into any dosage form which is suitable for systemic administration. For example, where the final compositions are to be administered by parenteral route, final dosages suitable for injection may be prepared in any manner known and acceptable to the skilled worker. Likewise, if administration to the patient is to be by peroral or intranasal route, suitable dosage forms may be prepared as is well known in the art. In the practice of this invention it is preferred to employ a parenteral route of administration to the patients being treated, although the other systemic routes also provide satisfactory results.

The invention may be further illustrated by the following examples.

EXAMPLE 1

Ten grams of grass pollen (*Lolium Perenne*) was extracted three times with a buffered aqueous phosphate solution. The solvent extract thus obtained is discarded and the thus extracted pollen residue is then washed with distilled deionized water and then dried in a vacuum drier under mild conditions until the moisture content thereof is less than three percent. The dried residue thus obtained is then ground by milling to a fine powder and one mg. of said powder is combined with one ml. of a 0.9 saline solution and then sterilized to prepare and injectable composition of this invention.

EXAMPLE 2

One gram of the dried extracted pollen residue obtained in Example 1 is treated with 1000 ml. of a buffered aqueous phosphate solution to which 10 grams of $\beta$-propriolactone has been added. The suspension thus obtained is continually stirred for a period of 14 days at room temperature and at a constant pH of about 7.0. The suspension is continually monitored by gas liquid chromatography to determine the presence of free $\beta$-propriolactone therein. After 5 days, no free $\beta$-propriolactone is detected. The reaction is allowed to continue in order to remove the last traces of $\beta$-propriolactone if any, and after 14 days the resultant suspension is filtered and the residue thoroughly washed with distilled water after which the washed residue is dried and prepared for administration to patients as described in Example 1.

EXAMPLE 3

The immunogenicity of the products of this invention was determined by employment of the passive cutaneous reaction (PCR) test in guinea pigs as described by Siriganian, Manual of Clinical Immunology, American Society of Microbiology, 1976, pp. 603–615. The sera of immunized guinea pigs were 1:4 diluted and 0.1 ml. of the dilutions, commencing with 1:4 were injected intracutaneously on the flank side of the untreated test guinea pigs with the same dilution. After binding of the cytophilic antibodies for 3 hours a mixture of the soluble test allergen with 0.5 ml of 2% Evans blue dye in saline was injected intravenously in the test animals. The test allergen was administered to each animal in an amount which approached the therapeutic dose thereof for humans. Thirty minutes after administration the reaction in the test animals was measured. The results obtained are set forth in Table 1 below:

TABLE 1

| Test Allergen | | Average PCA-Titers |
|---|---|---|
| 1 mg. | Phleum pratense residue prepared as in Example 1 | 53 ± 27 |
| 0.7 mg. | Phleum pratense freeze dried extract | 46 ± 40 |
| 0.007 mg. | Phleum pratense freeze dried extract | 6 ± 8 |

The foregoing demonstrates that even though the concentration of allergen in the Phleum pratense residue is only about 1% of that of the extract it has the capacity to raise the same amount of specific antibody as a 1% composition of the extract does. Therefore, equivalent protection with reduced allergenicity is obtained with the product of this invention.

EXAMPLE 4

The relative allergenic potency of the products of this invention may be determined by measurement of histamine release in the whole blood of human patients. Blood is incubated with the product of this invention, or untreated allergen. The histamine released is measured fluorometrically. The minimal amount of material releasing 50% of histamine, compared with the histamine release at optimal concentration, is used for calculations. The difference in histamine release capacity between the product of Example 1 and the prior art product were determined and are set forth in Table 2:

TABLE 2

| Bloodsample | Differences between the product of Example 1 and soluble Phleum pratense allergen on a weight base factor |
|---|---|
| Patient A | 200,000 |
| Patient B | 15,000 |

The foregoing results demonstrate that the residue of Example 1 has at least 10,000 times less allergenic activity in comparison with prior art products and can therefore be expected to produce fewer allergenic reactions.

EXAMPLE 5

The procedure of Example 2 is followed except that equivalent amounts of formaldehyde, glutaraldehyde, phenol and urea are substituted for β-propiolactone with similar results being obtained.

EXAMPLE 6

The procedure of Example 1 is followed except that as starting material a sufficient amount of mold, animal epithelia and yeasts were substituted for the grass pollen to yield the desired respective residues which may then be put into suitable injectable compositions.

The invention may be variously otherwise embodied within the scope of the appended claims.

What is claimed is:

1. A method of preparing an immunogenic product useful in the therapeutic treatment of patients suffering from allergic conditions, and which product possesses reduced allergenic properties, which comprises extracting an allergenic product by treatment thereof with a suitable solvent selected from the group consisting of water, alcohol, glycerol, dimethyl sulfoxide and phenol, in which the allergens to be extracted are soluble, until most of the soluble allergens contained in said allergenic product are extracted therefrom, discarding the solute thus obtained, and recovering the extracted residue thereof which contains no more than 1:100 w/w of its original allergen content, to yield the desired immunogenic product.

2. An immunogenic product prepared in accordance with the method of claim 1.

3. A method of treating patients suffering from allergic conditions which comprises systemically administering to said patients a small but effective amount of the product of claim 2.

4. The method of claim 3 in which the method of administration is by parenteral administration.

5. A method of preparing an immunogenic product which comprises further treating the extracted residue of claim 1 with a ketone, aldehyde, phenol, urea, dialdehyde, lactone or other denaturing reactant to obtain the desired immunogenic product.

6. A method of preparing an immunogenic product useful in the therapeutic treatment of patients suffering from allergic conditions, and which product possess reduced allergenic properties, which comprises extracting an allergenic product by treatment thereof with a suitable solvent until most of the soluble antigens contained therein are extracted therefrom, discarding the solute thus obtained, recovering the extracted residue thereof which contains no more than 1:100 w/w of its original allergen content, and further treating said extracted residue with β-propiolactone, the weight ratio of β-propiolactone to said residue being between 1:1 and 1:100, and removing all said β-propiolactone to yield the desired final product.

7. A product prepared in accordance with the method of claim 6.

* * * * *